(12) United States Patent
Front et al.

(10) Patent No.: US 6,567,687 B2
(45) Date of Patent: May 20, 2003

(54) METHOD AND SYSTEM FOR GUIDING A DIAGNOSTIC OR THERAPEUTIC INSTRUMENT TOWARDS A TARGET REGION INSIDE THE PATIENT'S BODY

(76) Inventors: Yaron Front, 11/24 Mendel Zinger St., Haifa 34984 (IL); Gal Ben-David, HaZait 238, Mitzpe Adi 17940 (IL)

( * ) Notice: Subject to any disclaimer, the term of this patent is extended or adjusted under 35 U.S.C. 154(b) by 0 days.

(21) Appl. No.: 09/900,042

(22) Filed: Jul. 9, 2001

(65) Prior Publication Data

US 2001/0041835 A1 Nov. 15, 2001

Related U.S. Application Data

(60) Division of application No. 09/512,294, filed on Feb. 24, 2000, now Pat. No. 6,368,331, which is a continuation-in-part of application No. 09/253,779, filed on Feb. 22, 1999, now Pat. No. 6,173,201.

(51) Int. Cl.[7] .................................................. A61B 6/00
(52) U.S. Cl. ..................... 600/426; 600/429; 600/407; 600/414; 600/417
(58) Field of Search .......................... 607/130; 600/407, 600/411, 414, 417, 426, 427, 440, 429

(56) References Cited

U.S. PATENT DOCUMENTS

| | | | | |
|---|---|---|---|---|
| 4,945,914 A | * | 8/1990 | Allen | 606/54 |
| 5,448,073 A | | 9/1995 | Jeanguillaume | 250/363.02 |
| 5,603,318 A | * | 2/1997 | Heilbrun et al. | 600/427 |
| 5,672,877 A | | 9/1997 | Liebig et al. | 600/425 |
| 5,682,886 A | * | 11/1997 | Delp et al. | 600/406 |
| 5,695,501 A | * | 12/1997 | Carol et al. | 606/130 |
| 5,776,064 A | | 7/1998 | Kalfas | 600/414 |
| 5,842,990 A | | 12/1998 | Kraske | 600/437 |
| 5,871,013 A | | 2/1999 | Wainer et al. | 600/407 |
| 5,871,445 A | * | 2/1999 | Bucholz | 600/407 |
| 5,879,297 A | * | 3/1999 | Haynor et al. | 600/407 |
| 5,961,457 A | * | 10/1999 | Raylman et al. | 600/436 |
| 6,021,342 A | * | 2/2000 | Brabrand | 600/427 |
| 6,272,370 B1 | * | 8/2001 | Gillies et al. | 600/411 |

* cited by examiner

Primary Examiner—Carl Layno

(57) ABSTRACT

Method and system are presented for guiding a diagnostic or therapeutic instrument towards a correct target inside the patient's body. A combined image obtained by registering structural and functional images of at least a portion of the patient's body including the target is used together with a guiding device. The guiding device has an indicator associated with the instrument, and is operable for presenting data indicative of a position of a location on the instrument relative to any other point in the at least portion of the patient's body. The guiding device is connectable to a computer device displaying the combined image and operable thereby for guiding the instrument towards the target.

57 Claims, 6 Drawing Sheets

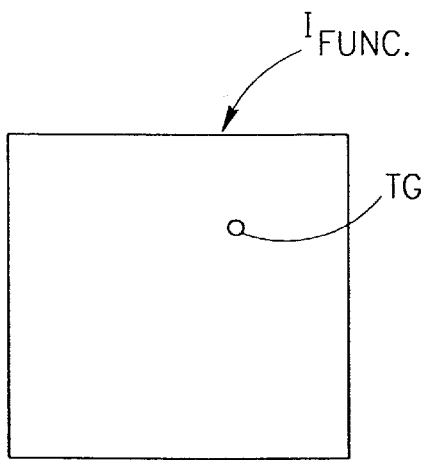
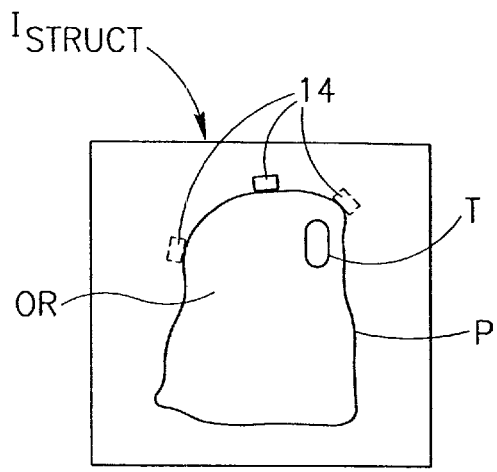
FIG.2A  FIG.2B
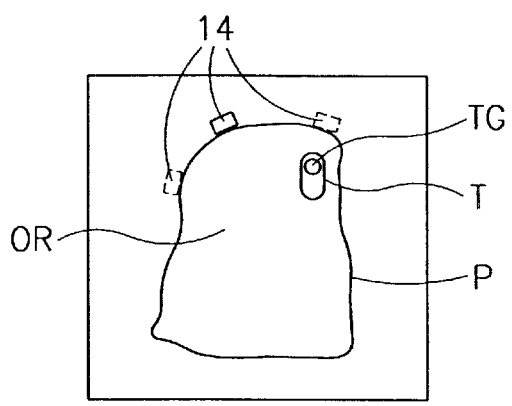
FIG.2C

METHOD AND SYSTEM FOR GUIDING A DIAGNOSTIC OR THERAPEUTIC INSTRUMENT TOWARDS A TARGET REGION INSIDE THE PATIENT'S BODY

This application is a division of U.S. application Ser. No. 09/512,294, filed Feb. 24, 2000, now U.S. Pat. No. 6,368,331 which is a continuation in part of U.S. application Ser. No. 09/253,779, filed Feb. 22, 1999, now U.S. Pat. No. 6,173,201.

FIELD OF THE INVENTION

The present invention is generally in the field of the diagnosis and treatment of ailments such as cancer, and relates to a method and system for guiding a diagnostic or therapeutic instrument towards a target region inside the patient's body.

BACKGROUND OF THE INVENTION

Diagnostic and therapeutic techniques aimed at diagnosing and treating cancerous tumors are known and widely used. Some of them involve the insertion of an instrument such as a needle, from outside the patient into a tumor that is suspected of being cancerous. For example, a biopsy needle commonly is inserted into a tumor to withdraw a tissue sample for biopsy. In brachytherapy, a radioisotope is placed at the tip of a needle, and the tip of the needle is inserted into the tumor to deliver radiation to the tumor with minimal irradiation of the surrounding healthy tissue. Although not common in medical practice, chemotherapeutic agents also may be injected into the tumor using a needle. Such needles are often inserted into the patient utilizing a series of structural images of the patient, such as ultrasound images, images obtained with Magnetic Resonance Imaging (MRI) or Computed Tomography (CT) techniques. These images are acquired before and during the insertion of the instrument, to verify that the instrument is being directed towards the correct target and is bypassing organs such as blood vessels, which should not be penetrated by the instrument.

Since a tumor may include both cancerous tissue and non-cancerous tissue, it is important to be able to direct an instrument specifically to a cancerous portion of a tumor, and to avoid misdiagnosis from the non-cancerous portion of a tumor. In the case of a biopsy, the needle should be directed towards the portion of the tumor that is most likely to be cancerous. In the case of brachytherapy, the needle should be directed towards the cancerous portion of the tumor. Structural imaging modalities, such as CT and MRI, that have enough spatial accuracy and resolution to distinguish and resolve tumors, are nevertheless unable to differentiate cancerous tissue from non-cancerous tissue. Functional imaging modalities, including tomographic nuclear imaging modalities, such as Single Photon Emission Computed Tomography (SPECT) and Positron Emission Tomography (PET), can distinguish cancerous tissue from non-cancerous tissue, but lack the spatial accuracy and resolution that is needed for the accurate positioning of instruments such as biopsy needles and brachytherapy needles.

Techniques for registering a functional image with a structural image to produce a combined image have been developed, and are disclosed, for example in the following publications: M. W. Vannier and D. E. Gayou, "Automated registration of multimodality images", *Radiology*, vol. 169 pp. 860–861 (1988); J. A. Correia, "Registration of nuclear medicine images, *J. Nucl. Med.*, vol. 31 pp. 1227–1229 (1990); J-C Liehn, A. Loboguerrero, C. Perault and L. Demange, "superposition of computed tomography and single photon emission tomography immunoscinigraphic images in the pelvis: validation in patients with colorectal or ovarian carcinoma recurrence", *Eur. J. Nucl. Med.*, vol. 19 pp. 186–194 (1992); F. Thomas et al., "Description of a prototype emission transmission computed tomography imaging system", *J. Nucl. Med.*, vol. 33 pp. 1881–1887 (1992); D. A. Weber and M. Ivanovic, "Correlative image registration", *Sem. Nucl. Med.*, vol. 24 pp. 311–323 (1994); and Hasegawa et al., U.S. Pat. No. 5,376,795. All six of these prior art documents are incorporated herein by reference for all purposes as if fully set forth herein. In principle, a sequence of such combined images could be used to direct an instrument to the cancerous portion of a tumor. In practice, the multiple imaging sessions and registrations that this would require make this solution impractical and possibly dangerous.

Stereotaxis is a known technique for localizing a region inside the body of a patient from outside the body of the patient, and for directing an instrument such as a needle, or a narrow beam of therapeutic radiation, to the target region. The degree of accuracy obtained from stereotaxis is relatively high, so this technique has been considered useful mainly on the brain and the breast. In stereotactic surgery of the brain, a CT localization frame is attached rigidly to the head of a patient and a CT image of the patient's brain is acquired with the CT localization frame in place. The position of the CT localization frame in the CT image is used to position the patient with respect to a surgical instrument utilizing a source of radiation so that the beam or beams of radiation intersects the desired target. Note that the CT localization frame is removed from the patient's head before the therapeutic irradiation commences.

Additionally, in order to access a correct location inside a patient's body with a diagnostic or therapeutic instrument, it is desirable to have exact information on the physical dimensions of the instrument. Using existing tools, such information can be obtained by one of the following means: prompting the user to enter all relevant physical dimensions; keeping a software library of known instruments and prompting the user for a specific model type; or prompting the user to perform a series of actions with a calibration device. Needless to say, these are cumbersome and time-consuming procedures, and require caregiver assistance.

SUMMARY OF THE INVENTION

There is accordingly a need in the art to facilitate the technique of accessing a correct target region inside the patient's body with a diagnostic or therapeutic instrument, aimed at diagnosis and therapy purposes, by providing a novel method and system for guiding the instrument towards the target region, which is not necessarily located in the head or breast.

It is a major feature of the present invention to provide such a method that utilizes a combined image of at least a portion of the patient's body including a target region, which image is obtained by registering a high-resolution structural image and a relatively low-resolution functional image of this portion of the patient's body.

It is a further feature of the present invention to provide such a system that utilizes a guiding device having an indicator associated with a diagnostic or therapeutic instrument for presenting data indicative of a position of the indicator relative to any other point in the chosen portion of the patient's body.

The main idea of the present invention consists of the utilization of a combined image, obtained by registering structural and functional images of at least a portion of the patient's body including a target region, for guiding an instrument (diagnostic or therapeutic) towards the target. The structural and functional images are obtained using, respectively, structural and functional modalities, namely suitable known techniques, and the combined image is obtained by using any known suitable technique, for example, those disclosed in the above publications.

As used herein, the term "target" refers to a structurally discrete portion in the patient's body, such as an organ or a tumor, that is suspected of containing disease (e.g., cancerous tissue). This diseased tissue (target) is surrounded by healthy tissues (e.g., non-cancerous tissue).

As used herein, the term "instrument" refers to a diagnostic or treatment instrument that can access and, if desired, be inserted into the target from outside the patient for the purpose of either diagnosis or treatment of a disease. Typical examples of such instruments include biopsy needles and needles for brachytherapy and chemotherapy.

According to one broad aspect of the present invention, there is provided a method for guiding an instrument towards a correct target inside the patient's body, the method comprising the steps of:

(i) providing an image of at least a portion of the patient's body including said target, wherein said image presents a combined image of registered structural and functional images of said at least portion of the patient's body;

(ii) providing data indicative of a position of a location on the instrument relative to any other point in said at least portion of the patient's body; and (iii) directing the instrument to said target.

To provide the combined image, the structural and functional images are obtained with, respectively, structural and functional modalities and registered. While directing the instrument towards the target, at least one additional image of the at least portion of the patient's body is preferably acquired with at least one of structural or functional modalities, for obtaining at least one additional combined image. Several additional images may be periodically or continuously acquired, and consequently, several additional combined images be obtained.

The structural and functional images used for obtaining the combined image may be, respectively, high-resolution and relatively low resolution. The resolution of 3–5 mm pixel size is considered to be low, and that of less than 1 mm pixel size is considered to be high resolution. In this case, the at least one additional image may be a low-resolution functional image or relatively higher resolution structural images (the so-called "medium-resolution" structural image). Alternatively, the structural and functional images used for obtaining the combined image may each be of a low resolution, in which case the at least one additional image is acquired with high-resolution structural modality.

To provide the data indicative of the relative position of the instrument, a guiding device is used having an indicator associated with the instrument.

The guiding device may comprise a frame attachable to the patient's body and a stereotactic guide. The indicator is in the form of at least three markers on the frame. In this case, to provide the combined image, the following steps are performed. The frame is rigidly secured to the patient, and then the high-resolution structural image is acquired using a high-resolution structural imaging modality, such as CT or MRI. This high-resolution structural image includes at least the portion of the patient's body. The markers are used by taking a series of structural images that covers all of them, since they are located in different planes. To acquire the functional image to be registered with the so-obtained high-resolution structural image, a suitable radiopharmaceutical, that is taken up preferentially by cancerous tissue (i.e., target), is injected into the patient, and the portion of the patient's body that was imaged with the structural modality is again imaged using a lower-resolution functional imaging modality that records radiation emitted by the radiopharmaceutical to acquire an image of the target. The structural image and the functional image are then registered to provide the combined image that shows the relative location of the target relative to other elements in the combined image. In other words, the combined image shows which part of a tumor mass seen in the structural image contains cancer, and where the cancerous areas are located on the high-resolution structural image.

Prior to performing step (iii), the stereotactic guide is rigidly attached to the frame. Since the position of the target (e.g., cancerous tissue) relative to the frame is known, the position of the target relative to the stereotactic guide is also known. The stereotactic guide then is used, under computer control, to guide the instrument, such as a biopsy needle or a brachytherapy needle, to the target, with reference to the pixels of the combined image that represent the markers and the target. The trajectory of the instrument is programmed in advance so that the instrument does not penetrate organs, such as vascular structures, that should not be penetrated.

According to another broad aspect of the invention, there is provided a method for accessing a target in a patient's body with an instrument, the method comprising the steps of:

(a) providing a guiding device having a frame to be secured to the patient and a stereotactic guide assembly, wherein the frame carries an indicator in the form of at least three markers;

(b) rigidly securing said frame to the patient;

(c) imaging at least a portion of the patient's body including the target, using a structural imaging modality, to produce a structural image of the at least portion of the patient's body and at least one of the markers, and acquiring a series of images to image all the markers and estimate their location in said structural image;

(d) imaging the at least portion of the patient's body using a functional imaging modality to produce a functional image of the at least portion of the patient's body; and (e) registering the functional image with the structural image to produce a combined image, (f) rigidly attaching said stereotactic guide assembly to said frame, and (g) directing the instrument to the target, using the stereotactic guide, with reference to said markers as imaged in the combined image.

According to another embodiment of the invention, the guiding device is a so-called tracking system composed of a guiding reference unit providing data indicative of space coordinates of the indicator that is in the form of a sensor attachable to the instrument at its handle portion, and a guiding controller. The latter is interconnected between the indicator and the guiding reference, and is connected to a computer device displaying the combined image. Such a tracking system may be of any known type, e.g., magnetic, optical, inertial, sound-waves, GPS. The construction and operation of the tracking system are known per se, and do not form part of the present invention. Therefore, the operation of the tracking system does not need to be specifically described, except to note the following. The controller is capable of tracking the position of a sensor and obtaining the information indicative of six degrees of freedom (i.e., 3 position coordinates and 3 rotation angles). The controller is installed with suitable hardware and is operated by suitable software for performing a signal processing technique and generating data indicative of the sensor's position in the coordinate space defined by the guiding reference. The computer device analyzes this data to generate a graphic representation of instrument location on the structural or functional image, or direction instructions for guiding the instrument towards the target.

Magnetic tracking systems are based on a magnetic/electronic field transmitter (guiding reference) and a relatively small receiver (indicator). Such a system may, for example, be the miniBIRD model, commercially available from Ascension Technology Corporation. Optical tracking systems apply a visual perception technique that observes either light reflected items or small light emitters, for example POLARIS models, commercially available from Northern Digital Inc.

Additionally, the indicator may comprise an identification electronic chip attached to the handle-portion of the instrument. This is actually a chip with an embedded application, such as a miniature electronic memory chip programmed during the manufacture of the specific instrument. The chip may be equipped with a transmitting utility generating and transmitting data indicative of the physical dimensions of the instrument or its corresponding code in accordance with a coded library. Alternatively or additionally, the chip may comprise a magnetic strip or a bar code to be read by a suitable reading head associated with the computer device.

According to another broad aspect of the present invention, there is provided a system for guiding an instrument towards a correct target inside the patient's body, the system comprising:
  a computer device for displaying an image of at least a portion of the patient's body including said target, wherein said displayed image presents a combined image of registered structural and functional images of said at least portion of the patient's body;
  a guiding device having an indicator associated with said instrument for presenting data indicative of a position of a location on the instrument relative to any other point in said at least portion of the patient's body, said guiding device being connectable to said computer device and operable thereby for directing the instrument to said target.

Preferably, the system also comprises an additional imaging modality capable of acquiring at least one of structural and functional images of said at least portion of the patient's body. This additional imaging modality is operable for acquiring at least one image, used for obtaining at least one additional combined image (a so-called "updated combined image"). This at least one additional combined image is utilized, while directing the instrument towards the target.

Although the scope of the present invention includes the diagnosis and treatment of any diseased tissue, the present invention is described below in terms of the primary application thereof, the diagnosis and treatment of cancer.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 2A to 2C schematically illustrate axial sections of a Ga-67, a CT and a combined image of a chest of a patient;

DETAILED DESCRIPTION OF A PREFERRED EMBODIMENT

Figure 1:
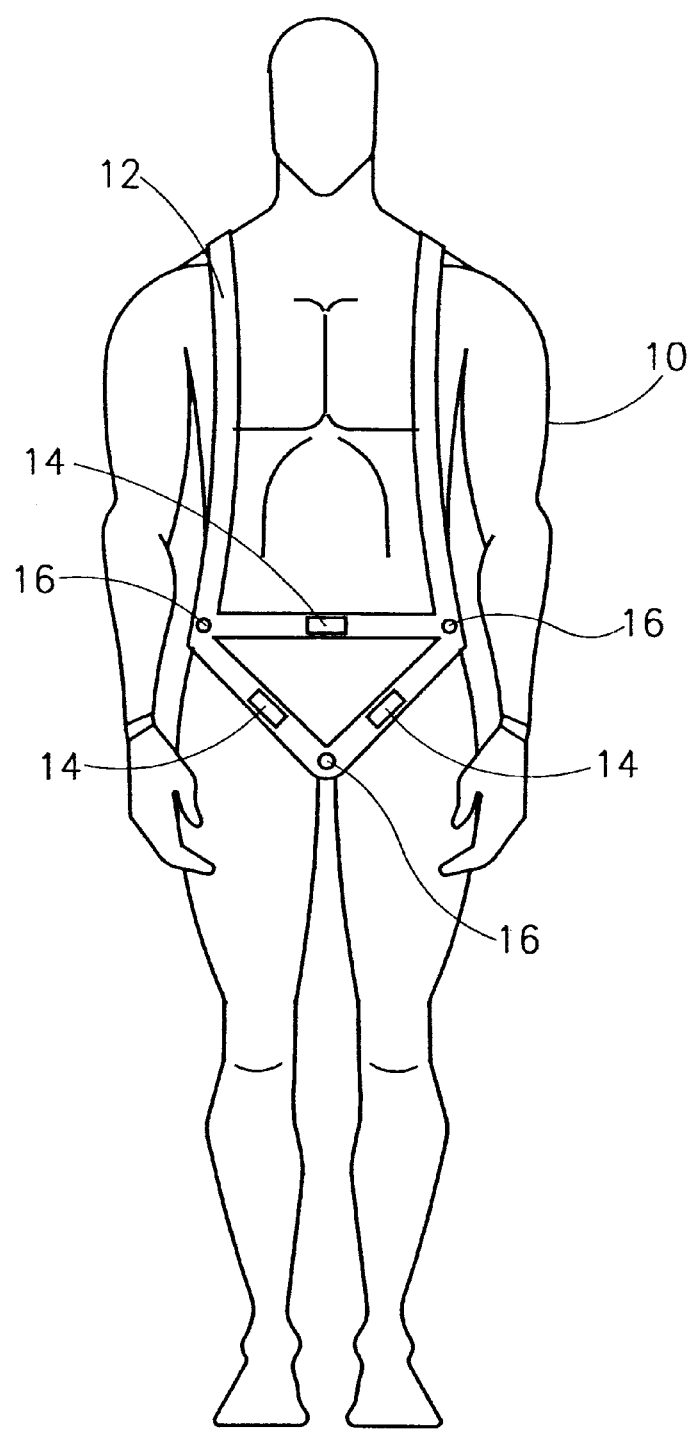
FIG. 1 shows a patient wearing a frame.
Figure 3:
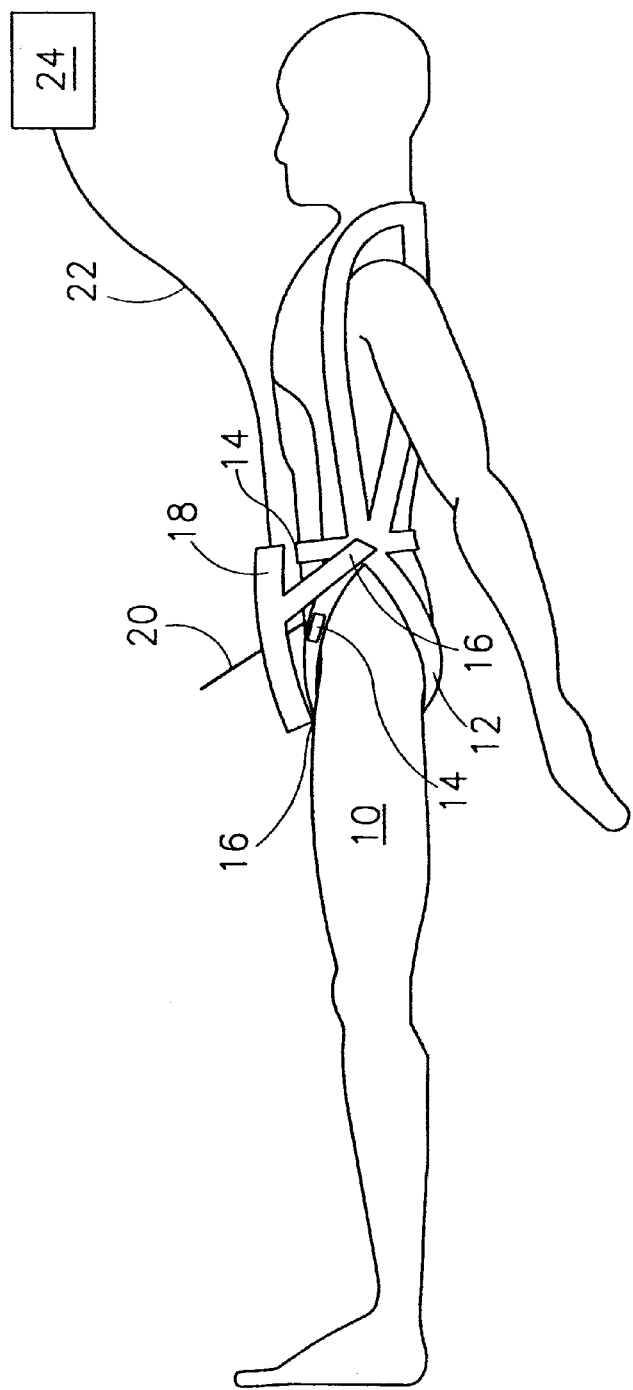
FIG. 3 shows the patient of FIG. 1 with a stereotactic guide attached to the frame.

Referring to FIGS. 1–3, there is illustrated one embodiment of the present invention utilizing a method of stereotactic diagnosis and treatment of diseased tissue. FIG. 1 shows a patient 10 wearing a rigid frame 12. By virtue of being snugly fitted to the shoulders, waist and groin of patient 10, frame 12 is rigidly secured to patient 10. Frame 12 bears thereon three markers 14 (constituting an indicator) that include a material that shows up well in a high-resolution structural image of the patient 10 and frame 12. For example, if CT is used for structural imaging, markers 14 are lead blocks. If MRI is used for structural imaging, markers 14 are hollow plastic blocks filled with a solution of Gd-DTPA. Frame 12 also bears three attachment points 16 for a stereotactic guide. A high-resolution structural image of the portion of patient 10 that contains the target is acquired while patient 10 wears frame 12 as shown in FIG. 1.

Three is the minimum number of markers 14 that is needed for accurately recording the relative positions of frame 12 and the internal tissues of patient 10 in three dimensions in the structural image. Markers 14 are shown in FIG. 1 as three blocks only for illustrational clarity. Any suitable marker geometry or form may be used, for example, vertical and diagonal rods, as are used in the BRW CT localization frame commercially available from Radionics. Inc., of Burlington Mass. and from Sofamor Danek, of Elektra, Sweden, for stereotactic treatment of the patient's brain. The positioning of markers 14 and attachment points 16 on frame 12 in FIG. 1 also is only illustrative, as an example of appropriate positions of markers 14 and attachment points 16 for treatment of the abdomen of patient 10.

Subsequent to or simultaneously with the acquisition of a high-resolution structural (e.g., CT or MRI) image of the portion of patient 10 that includes the target (while the patient wears the frame), a lower resolution functional (e.g., nuclear medicine) image of the same portion of patient 10 is acquired for the purpose of imaging the target in the entire portion imaged by the structural modality. If the disease under treatment is cancer, then the preferred imaging modality is nuclear imaging, and the patient is injected before imaging with a radiopharmaceutical that is preferentially taken up by cancerous tissue. Examples of such radiopharmaceuticals include Ga-67, Tc-99m MIBI, Tl-201, F-18 fluorodeoxyglucose and In-111 octreotide. The most preferred nuclear imaging modalities are tomographic modalities such as SPECT and PET. The functional and structural images then are registered, for example as described in the paper by Weber and Ivanovic cited above, to produce a combined image.

FIG. 2A is a schematic illustration of an axial section of a Ga-67 image $I_{func}$ of a chest of a cancer patient, showing a tumor T containing a lymphoma that constitutes the target TG to be accessed by an instrument (not shown). FIG. 2B is a schematic illustration of an axial section of a CT image $I_{struct}$ of the same patient's chest. A portion P of the patient's body including the tumor T is imaged. The target TG is not seen in the structural image $I_{struct}$, since there is typically no visual contrast in such image between the lymphoma and the rest of the tumor. What can be seen in such a structural image are organs and tissues, generally at OR, surrounding the tumor T (and consequently the target to be detected), and typically one of the markers 14 on the frame. Although three markers are presented in the drawings as seen in the structural image, two of them are shown in dotted lines, since the markers are located in different planes, and only one of them will be seen in such a sectional view. FIG. 2C is an axial section of a combined image $I_{com}$, showing the functional image $I_{func}$ of FIG. 2A registered on the structural image $I_{struct}$ of FIG. 2B. Any known suitable technique can be used for registering images of FIGS. 2A and 2B to obtain the combined image of FIG. 2C, for example the techniques described in the above-indicated publications. Biopsy and therapy directed towards the tumor should be aimed specifically at the lymphoma.

FIG. 3 shows patient 10 with a stereotactic guide 18 firmly and rigidly attached to frame 12 at attachment points 16, and with a diagnostic or therapeutic instrument 20, such as a biopsy needle or a brachytherapy needle, mounted in stereotactic guide 18 in its ready-for-insertion position to be inserted into the abdomen of patient 10 under the control of a computer device 24.

Computer 24 is equipped with suitable hardware and operated by suitable software for sending control signals, including the relevant Cartesian coordinates, to stereotactic guide 18 via suitable signal communication means, for example electrical connection such as a cable 22. It should be understood, although not specifically shown, that wireless connection could be used. Computer 24 also includes a suitable display mechanism, such as a video terminal, for displaying the combined image.

A physician programs the trajectory of instrument 22 in computer 24 in advance, with reference to the position of the target TG and the other internal organs OR of patient 10, and with reference to markers 14, as seen in the combined image $I_{com}$. Computer 24 is installed with suitable software that transforms data indicative of the coordinate system of the combined image, as defined by markers 14, into the coordinate system of stereotactic guide 18. This software is used to transform the coordinates of the trajectory, which is defined by the physician in the coordinate system of the combined image, into the coordinate system of stereotactic guide 18, to enable stereotactic guide 18 to steer instrument 20 along the desired trajectory. The physician designs the trajectory to avoid vascular structures and other organs that should not be penetrated by instrument 20.

To assist the physician in recognizing and avoiding vascular structures such as blood vessels, another functional image of the portion of patient 10 that includes the target is acquired, for the purpose of imaging the blood vessels. The preferred imaging modality for imaging vascular structures is Tc-99m labeled red blood cells SPECT. For this purpose, patient 10 is first injected with Tc-99m, to label the red blood cells of patient 10. The SPECT image of the vascular structures is registered with the structural image initially obtained and utilized in the initial combined image shown in FIG. 2C, and a resulting second combined image is displayed by computer 24 and is used by the physician in planning the trajectory of instrument 20 to avoid penetration of the imaged vascular structures.

Similarly, to assist the physician in recognizing and avoiding organs such as the kidneys, another functional image of the portion of patient 10 that includes the target is acquired. In the specific case of the kidneys, this second functional image is a SPECT image obtained using Tc-99 DMSA. The SPECT image of the organ or organs is registered with the structural image, and the resulting second combined image is displayed by computer 24 and is used by the physician in planning the trajectory of instrument 20 to avoid penetration of the imaged organs. To prevent errors in planning the trajectory of instrument 20, computer 24 is programmed to avoid penetration of blood vessels and organs with a high blood pool, and other organs that should not be penetrated, such as the gut, the kidneys, the pancreas and the heart.

It should be understood that more than one additional combined image can be obtained, the number of these additional images depending on a specific application, e.g., a target to be accessed. A physician himself decides how many updates of the initial combined images are needed for successfully guide the instrument towards the target.

In the above-described example of the present invention, the biopsy needle guidance utilizes the stereotactic guide assembly, with reference to the diseased portion of the patient's body and to the markers as imaged on the first combined image. In other words, in the above-described example, a guiding device is constituted by the frame with markers and by the stereotactic guide assembly. However, other guidance and motion tracking systems are suitable as well. Such systems are, but not limited to magnetic and optical systems.

Figure 4:
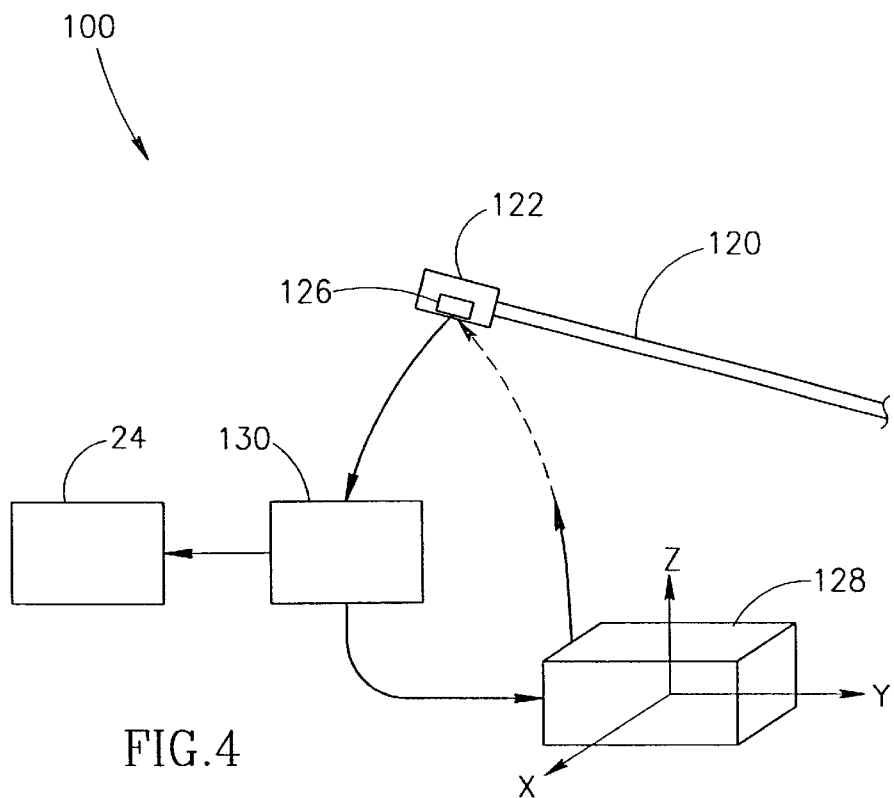
FIG. 4 illustrates the main constructional parts of a system according to another embodiment of the invention.

Reference is made to FIG. 4, illustrating the main components of a system, generally designated 100, according to another embodiment of the invention. System 100 is composed of an indicator 126 appropriately attached to a handle portion 122 of an instrument 120, a guiding reference unit 128 and a guiding controller 130 connected to the computer 24.

As indicated above, such a system may be of magnetic or optical kind, for example, commercially available from Ascension Technology Corporation and Northern Digital Inc., respectively. Generally speaking, the guiding reference unit 128 and the indicator 126 operate together to generate data indicative of the indicator position in a 6D coordinate space (3 position coordinates and 3 rotation angles) and transmit this data to the guiding controller 130. The latter transmits corresponding data to the computer device 24, which registers this data with the combined image to generate a graphic representation of the instrument's location on the structural or functional image or direction instructions for guiding the instrument 120 towards the target, as described above.

Figure 5:
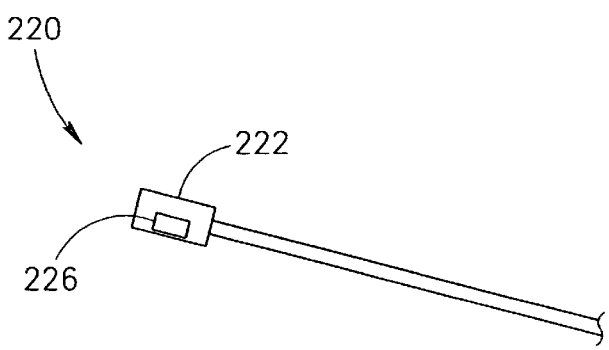
FIG. 5 illustrates another feature of the present invention suitable to be used in the embodiment of FIGS. 1 and 3, or the embodiment of FIG. 4.

Turning now to FIG. 5, there is illustrated an instrument 220 having a handle portion 222 formed with an identification chip 226. As indicated above, a major factor in the accuracy of the system of the kind specified is exact information on the physical dimensions of a diagnostic or therapeutic instrument associated with a guiding device. To this end, the diagnostic or therapeutic instrument 220 according to the invention is equipped with the chip 226 with an embedded application enabling the identification of the physical dimensions of the specific instrument. The chip provides data indicative of the instrument's physical parameters, which may be dimensions themselves, or coded data that can be identified by the software installed in the computer 24 (i.e., library storing information corresponding to various Serial Numbers of diagnostic and therapeutic instruments manufactured by various manufacturers). The computer 24 itself may have a special utility for communicating with the embedded application of the chip.

According to the present invention, diagnosis and/or treatment are performed with respect to an image of the target region in the patient's body that combines a high-resolution structural image, such as a CT or MRI image, with a lower resolution functional image, such as a nuclear image. The combined image may be used to assist the caregiver in locating the instrument with respect to the target. Pieces of materials that are clearly shown in one of the modalities may be used to gain information in the combined image. Such materials are, but not limited to, radioactive emitters that are clearly seen by means of the nuclear medicine image, and lead capsules that are highly visible in a CT image. Such pieces can be attached to known locations on the therapeutic instrument, thereby serving as indicators. These indicators are useful in the procedure navigation process, where the physician inserts the instrument toward the target. At the end of the procedure there is a verification phase, where the physician validates the location of the instrument with respect to the target. During the verification phase both the tissue and the highlight indicator are clearly seen in the combined image. This increases the degree of confidence that the procedure instrument was correctly applied.

Figure 6A:
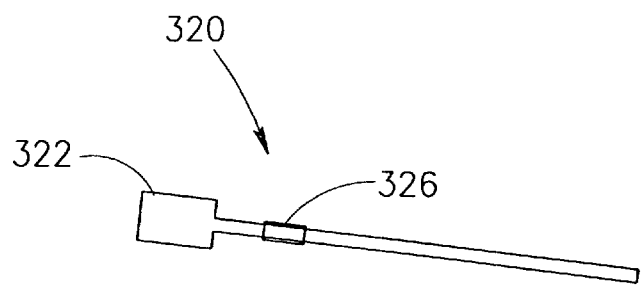
FIGS. 6a and 6b illustrate two more examples of an indicator suitable to be used in the present invention.

FIG. 6A shows the main principles of the above concept. Here, such an indicator 326 (e.g., radioactive emitters) is attached to a location on an instrument 320 close to its handle portion 322.

Figure 6B:
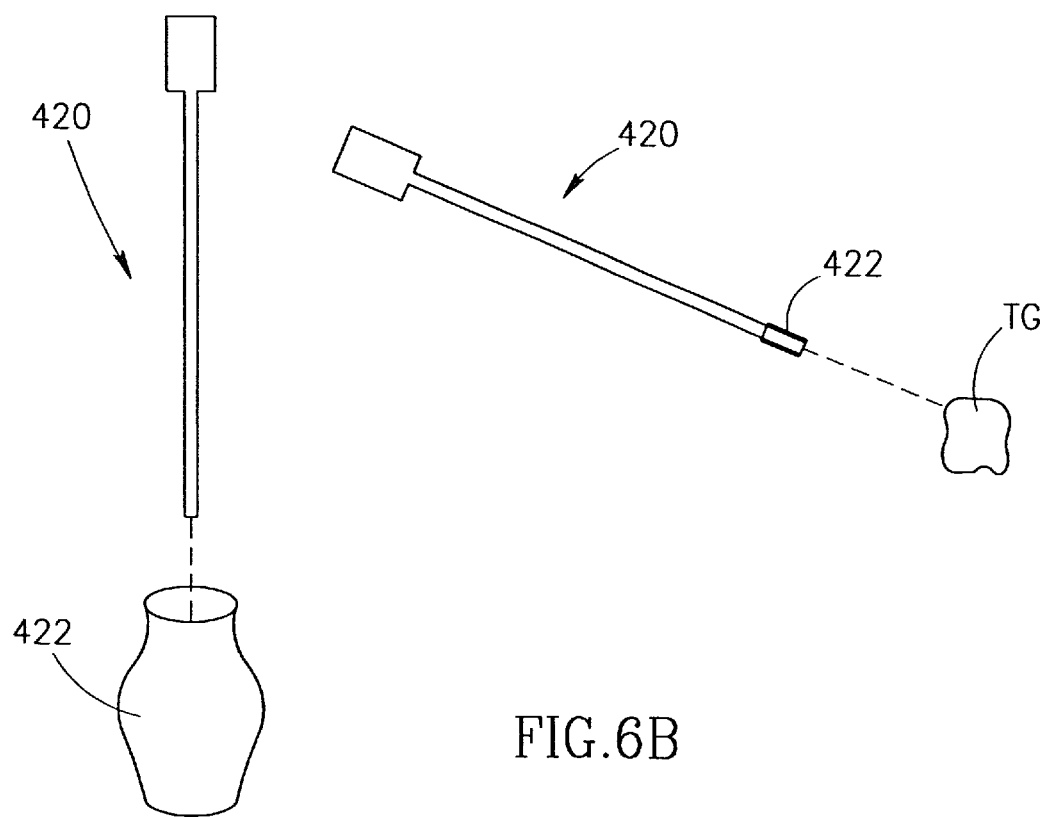

FIG. 6B illustrates an example where treatment of the target is needed. To this end, a therapeutic instrument 420 is at its distal end formed with a suitable material 422 that can be clearly seen in an image of one of the modalities to gain information in the combined image. Thus, the therapeutic instrument 420 is initially inserted by its distal end into a vessel containing material 422, and is then directed towards the target TG. Such materials are, but not limited to, radioactive materials that are clearly seen by means of the nuclear medicine image, and iodine that is highly visible in a CT image. The highlight material may also be mixed with the therapeutic chemical in advance. The highlight materials are injected together with therapeutic chemical substances and are used to track the absorption of the substances with respect to the tumor while minimizing damage to the surrounding healthy tissue.

As indicated above, diagnosis is performed with respect to an image of the target region of the patient that combines a high-resolution structural image, such as a CT or MRI image, with a lower resolution functional image, such as a nuclear image. For various reasons, a physician may prefer to perform the clinical procedure under single modality equipment that may be different from the equipment originally used to make the combined image. In this case, the combined image is made of a relatively high-resolution structural image, lower resolution functional image, and another image that may be either structural or functional of a different resolution. For example, a low-resolution PET image may be combined with a medium-resolution CT image, which images are collected during a preliminary diagnostic procedure. The actual procedure is carried out under a high-resolution CT or MRI imaging, that was designed for such procedures.

Figure 7:
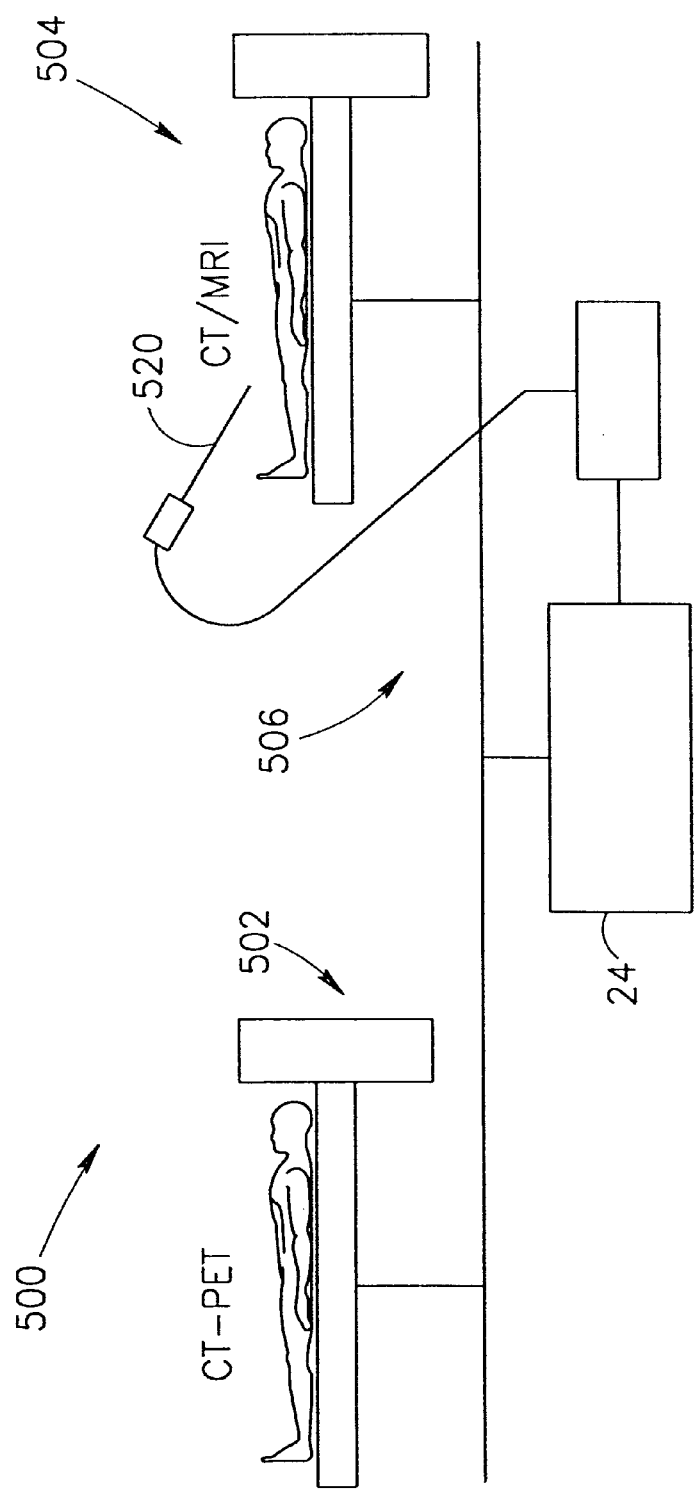
FIG. 7 illustrates some more features of a method and system according the invention.

The above concept is schematically illustrated in FIG. 7, showing a system 500 utilizing low-resolution CT imaging modality (as compared to that used during the instrument insertion procedure) and low-resolution PET imaging modality, generally at 502, that obtain a combined image of a portion of the patient's body including a target and transmit data to a computer device 24 and to a high-resolution CT modality 504 through a computer network. A guiding device 506 associated with a diagnostic or therapeutic instrument 520 and coupled to the computer 24, is used for guiding the instrument towards the target with simultaneous image acquisition with the high-resolution CT imaging modality 504.

Those skilled in the art will readily appreciate that various modifications and changes can be applied to the preferred embodiment of the invention as hereinbefore described without departing from its scope defined in and by the appended claims.

What is claimed is:

1. A medical imaging system, comprising:
   a rigid frame, which includes:
      fittings for snugly securing said frame to a patient's body; and
      at least three fiducial marks, arranged at different locations, on said frame;
   a three-dimensional, first structural imaging modality, adapted for imaging different densities within the patient's body and adapted to detect said at least three fiducial marks, for defining a three-dimensional coordinate system;
   a three-dimensional, first functional imaging modality, adapted for imaging radioactively tagged pharmaceuticals, injected to the patient and distributed in the patient's body due to physiological activities, thus adapted to detect said target, wherein said first functional imaging modality is spatially registered to said three-dimensional coordinate system; and
   a computer device, for receiving input from said first structural and functional imaging modalities and for simultaneously displaying both, superimposed.

2. The system of claim 1, wherein said first structural imaging modality is selected from the group consisting of CT, MRI, Ultrasound and planar X-Ray imaging.

3. The system of claim 1, wherein said first structural imaging modality is MRI.

4. The system of claim 3, wherein said fiducial marks are formed as hollow plastic containers filled with a solution of Gd-DTPA.

5. The system of claim 1, wherein said first structural imaging modality is CT.

6. The system of claim 5, wherein said fiducial marks are formed of lead.

7. The system of claim 1, wherein said first functional imaging modality is nuclear imaging, selected from the group consisting of gamma camera, PET and SPECT.

8. The system of claim 1, wherein said system comprises at least one additional, three-dimensional, functional imaging modality, spatially registered to said three-dimensional coordinate system.

9. The system of claim 8, wherein said computer device is adapted for simultaneously displaying an image of said at least one additional functional imaging modality, superimposed on said first structural imaging modality.

10. The system of claim 8, wherein said at least one additional functional imaging modality is adapted for imaging at least one body organ which should not be penetrated.

11. The system of claim 8, wherein said at least one additional functional imaging modality is adapted for imaging at least one organ selected from the group consisting of blood vessels, the kidneys, the gut, the pancreas, the heart, a breast, the prostate, the thyroid, the lungs, the brain, a lymph Node, bones, ovaries, the colon, the rectum.

12. The system of claim 1, and further including at least one additional, structural imaging modality of a lower resolution than said first structural imaging modality, spatially registered to said three-dimensional coordinate system.

13. The system of claim 1, wherein said at least three fiducial marks are arranged on different planes, with respect to said three-dimensional coordinate system.

14. A system for guiding an instrument towards a target inside a patient's body, said system comprising:
    a rigid frame, which includes:
        fittings for snugly securing said frame to the patient's body; and
        at least three fiducial marks, arranged at different locations, on said frame;
    a three-dimensional, first structural imaging modality, adapted for imaging different densities within the patient's body and adapted to detect said at least three fiducial marks, for defining a three-dimensional coordinate system;
    a three-dimensional, first functional imaging modality, adapted for imaging radioactively tagged pharmaceuticals, injected to the patient and distributed in the patient's body due to physiological activities, thus adapted to detect said target, wherein said first functional imaging modality is spatially registered to said three-dimensional coordinate system;
    a computer device, for receiving input from said first structural and functional imaging modalities and for simultaneously displaying both, superimposed; and
    a stereotactic guide, selectively attached to said rigid frame, so as to be spatially registered to said three-dimensional coordinate system, said stereotactic guide having an instrument mounted thereon, for guiding said instrument to said target, under the control of said computer device.

15. The system of claim 14, wherein said first structural imaging modality is selected from the group consisting of CT, MRI, Ultrasound and planar X-Ray imaging.

16. The system of claim 14, wherein said first structural imaging modality is MRI.

17. The system of claim 14, wherein said fiducial marks are formed as hollow plastic containers filled with a solution of Gd-DTPA.

18. The system of claim 14, wherein said first structural imaging modality is CT.

19. The system of claim 18, wherein said fiducial marks are formed of lead.

20. The system of claim 14, wherein said first functional imaging modality is nuclear imaging, selected from the group consisting of gamma camera, PET and SPECT.

21. The system of claim 14, wherein said system comprises at least one additional, three-dimensional, functional imaging modality, spatially registered to said three-dimensional coordinate system.

22. The system of claim 21, wherein said computer device is adapted for simultaneously displaying an image of said at least one additional functional imaging modality, superimposed on said first structural imaging modality.

23. The system of claim 21, wherein said at least one additional functional imaging modality is adapted for imaging at least one body organ which should not be penetrated.

24. The system of claim 21, wherein said at least one additional functional imaging modality is adapted for imaging at least one organ selected from the group consisting of blood vessels, the kidneys, the gut, the pancreas, the heart, a breast, the prostate, the thyroid, the lungs, the brain, a lymph Node, bones, ovaries, the colon, the rectum.

25. The system of claim 14, said system comprising at least one additional three-dimensional, structural imaging modality, of a lower resolution than said first structural imaging modality, spatially registered to said three-dimensional coordinate system.

26. The system of claim 14, wherein said at least three fiducial marks are arranged on at least two different planes, with respect to said three-dimensional coordinate system.

27. The system of claim 14, wherein said stereotactic guide includes an optical guiding system.

28. The system of claim 14, wherein said a stereotactic guide includes a magnetic guiding system.

29. The system of claim 14, wherein said instrument includes an indicator, in communication with said computer device, for generating and transmitting data, indicative of said instrument's position, in a six-dimensional space.

30. The system of claim 14, wherein said instrument includes an identification chip, in communication with said computer device, for providing exact information on the physical dimensions of said instrument.

31. The system of claim 14, wherein said instrument includes a highlight mark.

32. The system of claim 31, wherein said highlight mark includes a lead capsule, which is visible on a CT image.

33. The system of claim 31, wherein said highlight mark includes iodine, which is visible on a CT image.

34. The system of claim 33, wherein said iodine is mixed and injected with a therapeutic solution, at said target.

35. The system of claim 31, wherein said highlight mark includes a radioactive material, which is visible on a nuclear image.

36. The system of claim 35, wherein said radioactive material is mixed and injected with a therapeutic solution.

37. A system for guiding an instrument towards a target inside a patient's body, said system comprising:
    a rigid frame, which includes:
        fittings for snugly securing said frame to the patient's body; and
        at least two fiducial marks, arranged at different locations, on a plane of said frame;
    a two-dimensional, first structural imaging modality, adapted for imaging different densities within the patient's body and adapted to detect said at least two fiducial marks, for defining a two-dimensional coordinate system;
    a two-dimensional, first functional imaging modality, adapted for imaging radioactively tagged pharmaceuticals, injected to the patient and distributed in the patient's body due to physiological activities, thus adapted to detect said target, wherein said first functional imaging modality is spatially registered to said two-dimensional coordinate system;
    a computer device, for receiving input from said first structural and functional imaging modalities and for simultaneously displaying both, superimposed; and
    a guide, selectively attached to said rigid frame, so as to be spatially registered to said coordinate system, said guide having an instrument mounted thereon, for guiding said instrument to said target, under the control of said computer device.

38. The system of claim 37, wherein said first structural imaging modality is MRI.

39. The system of claim 38, wherein said fiducial marks are formed as hollow plastic containers filled with a solution of Gd-DTPA.

40. The system of claim 37, wherein said first structural imaging modality is CT slices.

41. The system of claim 40, wherein said fiducial marks are formed of lead.

42. The system of claim 37, wherein said first functional imaging modality is nuclear imaging.

43. The system of claim 37, wherein said system comprises at least one additional, two-dimensional, functional imaging modality, spatially registered to said coordinate system.

44. The system of claim 43, wherein said computer device is adapted for simultaneously displaying an image of said at least one additional functional imaging modality, superimposed on said first structural imaging modality.

45. The system of claim 43, wherein said at least one additional functional imaging modality is adapted for imaging at least one body organ which should not be penetrated.

46. The system of claim 43, wherein said at least one additional functional imaging modality is adapted for imaging at least one organ selected from the group consisting of blood vessels, the kidneys, the gut, the pancreas, the heart, a breast, the prostate, the thyroid, the lungs, the brain, a lymph Node, bones, ovaries, the colon, the rectum.

47. The system of claim 37, said system comprising at least one additional two-dimensional, structural imaging modality, of a lower resolution than said first structural imaging modality, spatially registered to said coordinate system.

48. The system of claim 37, wherein said guide includes an optical guiding system.

49. The system of claim 37, wherein said guide includes a magnetic guiding system.

50. The system of claim 37, wherein said instrument includes an indicator, in communication with said computer device, for generating and transmitting data, indicative of said instrument's position, in a six-dimensional space.

51. The system of claim 37, wherein said instrument includes an identification chip, in communication with said computer device, for providing exact information on the physical dimensions of said instrument.

52. The system of claim 37, wherein said instrument includes a highlight mark.

53. The system of claim 52, wherein said highlight mark includes a lead capsule, which is visible on a CT image slice.

54. The system of claim 52, wherein said highlight mark includes iodine, which is visible on a CT image slice.

55. The system of claim 54, wherein said iodine is mixed and injected with a therapeutic solution, at said target.

56. The system of claim 52, wherein said highlight mark includes a radioactive material, which is visible on a nuclear image.

57. The system of claim 56, wherein said radioactive material is mixed and injected with a therapeutic solution.

* * * * *